United States Patent [19]

Townsend et al.

[11] Patent Number: 4,590,310
[45] Date of Patent: May 20, 1986

[54] PROCESS FOR THE PREPARATION OF 2,2,2-TRIFLUOROETHANOL

[75] Inventors: Palmer W. Townsend, Berkeley Heights; Chialang Huang, Edison; Gerald G. Vernice, Nutley, all of N.J.

[73] Assignee: The BOC Group, Inc., Montvale, N.J.

[21] Appl. No.: 636,882

[22] Filed: Aug. 2, 1984

[51] Int. Cl.$^4$ .............................................. C07C 31/38
[52] U.S. Cl. .................................................... 568/842
[58] Field of Search ........................................ 568/842

[56] References Cited

U.S. PATENT DOCUMENTS

| | | |
|---|---|---|
| 2,868,846 | 1/1959 | Lawlor et al. . |
| 3,356,746 | 12/1967 | Anello et al. . |
| 3,356,747 | 12/1967 | Anello et al. . |
| 3,970,710 | 7/1976 | Wolownik . |
| 4,311,863 | 1/1982 | Gunprecht . |
| 4,396,784 | 8/1983 | Johnson et al. . |
| 4,434,297 | 2/1984 | Astrologes . |
| 4,489,211 | 12/1984 | Ogura et al. .......... 568/842 |

FOREIGN PATENT DOCUMENTS 58-134043 2/1983 Japan .................... 568/842

OTHER PUBLICATIONS

Chem. Abs., 100, 341382, (1984).
Chem. Abs., 99, 212148y, (1983).
Chem. Abs., 85, 123333y, (1976).
Chem. Abs., 69, 51575y, 1968, (Zech 124981).

*Primary Examiner*—Howard T. Mars
*Attorney, Agent, or Firm*—Arnold H. Krumholz; Roger M. Rathbun; Larry R. Cassett

[57] ABSTRACT

A continuous process is disclosed for preparing 2,2,2-trifluoroethanol from 2-halo-1,1,1-trifluoroethane, preferably 2-chloro-1,1,1-trifluoroethane. In the process, 2-halo-1,1,1-trifluoroethane, a carboxylic acid salt and an hydroxylated compound such as water are continuously provided to a reaction mixture in a reactor. The 2-halo-1,1,1-trifluoroethane, the carboxylic acid salt and the hydroxylated compound are reacted therein at a reaction pressure at or above the autogenously developed pressure and at a reaction temperature of from about 223° C. to about the critical temperature of the hydroxylated compound. At least a portion of the reaction product mixture is continuously withdrawn from the reactor and unreacted 2-halo-1,1,1-trifluoroethane is separated therefrom. The separated unreacted 2-halo-1,1,1-trifluoroethane is recycled as part of the 2-halo-1,1,1-trifluoroethane provided to the reaction mixture. The 2,2,2-trifluoroethanol is recovered from the reaction product mixture.

54 Claims, 2 Drawing Figures

PROCESS FOR THE PREPARATION OF 2,2,2-TRIFLUOROETHANOL

BACKGROUND OF THE INVENTION

The present invention relates to processes for preparing 2,2,2-trifluoroethanol. In particular, the invention relates to continuous processes for preparing such product.

2,2,2-trifluoroethanol is a starting material for the synthesis of various products, including the inhalation anesthetic isoflurane ($CF_3CHClOCHF_2$). Various processes have been disclosed for preparing 2,2,2-trifluoroethanol. For example, in Lawlor et al., U.S. Pat. No. 2,868,846, a process is disclosed in which 2,2,2-trifluoroethanol may be made by heating 2-chloro-1,1,1-trifluoroethane in a reaction medium which includes an hydroxylated solvent, with the reaction medium being maintained at a pH of between 3 and 10, for example, by having dissolved therein a salt of a weak acid. Lawlor et al. say that to bring about reaction, the reaction mixture is heated preferably at a temperature in the range of 175° to 300° C. and preferably under the autogenously developed pressure. All of the reactions specifically disclosed in the Lawlor et al. patent are performed in a stirred autoclave on a batch basis. Also, the products and unreacted 2-chloro-1,1,1-trifluoroethane in the Lawlor et al. examples are either directly distilled after substantial depressurization from the autoclave or the liquid product is fractionated with the 2-chloro-1,1,1-trifluoroethane and 2,2,2-trifluoroethanol being separately collected. Similar processes conducted on a batch basis are disclosed in Chemical Abstracts, Vol. 69, Abst. No. 51575y (1968); Chemical Abstracts, Vol. 99, Abst. No. 212148y (1983); and Chemical Abstracts, Vol. 100, Abst. No. 34138z (1984).

A two-stage method for preparing 2,2,2-trifluoroethanol is disclosed in Astrologes, U.S. Pat. No. 4,434,297. In the Astrologes process, 2-chloro-1,1,1-trifluoroethane is reacted with an alkali metal salt of a carboxylic acid in a substantially anhydrous aprotic solvent, e.g., N-methyl-2-pyrrolidone, to form the carboxylic acid ester of 2,2,2-trifluoroethanol and an alkali metal chloride. This ester is then reacted with an hydroxide or a basic salt of an alkali metal in water to form 2,2,2-trifluoroethanol and the alkali metal salt. The alkali metal salt is disclosed as then being recycled for further reaction. The Astrologes patent suggests that his process can be run continuously but gives no details in that connection. The patent makes clear that the Astrologes process should be performed at temperatures below 200° C. and that it is desirable to maintain pressures below about 500 psig as Astrologes' reaction progresses. Moreover, all of Astrologes' examples indicate that long reaction times, typically of from 3 to 10 hours and longer are required.

Other more remote methods to produce 2,2,2-trifluoroethanol include, e.g., catalytic hydrogenation of: trifluoroacetic acid; trifluoroacetyl chloride; 2,2,2-trifluoroethyl trifluoroacetate; or trifluoroacetic anhydride. See, for example, U.S. Pat. Nos. 3,356,746, 3,356,747, 3,970,710 and 4,396,784 and Chemical Abstracts, Vol. 85, Abst. No. 123333y. Also, Gumprecht, U.S. Pat. No. 4,311,863, discloses that 2,2,2-trifluoroethanol can be a by-product of the reaction of 2-chloro-1,1,1-trifluoroethane or 2-bromo-1,1,1-trifluoroethane with alkali metal fluoride in the presence of water.

It is highly desirable to provide a process in which 2,2,2-trifluoroethanol can be prepared on a continuous basis in high yields by an efficient process and with a relatively simple way of recycling unreacted 2,2,2-trifluoro-1-haloethane and optionally the organic acid salt or acid form thereof.

SUMMARY OF THE INVENTION

It has now been found that an improved process can be provided for preparing 2,2,2-trifluoroethanol economically, efficiently and in high yields. Specifically, the applicants have discovered a continuous process for preparing 2,2,2-trifluoroethanol in which 2-halo-1,1,1-trifluoroethane, a salt of a carboxylic acid and an hydroxylated compound are provided to a reaction mixture in a reactor. The 2-halo-1,1,1-trifluoroethane is reacted with the carboxylic acid salt and the hydroxylated compound in the reactor at a reaction pressure at or above the autogenously developed pressure and at a reaction temperature of from about 223° C. to about the critical temperature of the hydroxylated compound to thereby produce a reaction product mixture containing 2,2,2-trifluoroethanol. At least a portion of the reaction product mixture is continuously withdrawn from the reactor and unreacted 2-halo-1,1,1-trifluoroethane is separated from the withdrawn reaction product mixture. The separated 2-halo-1,1,1-trifluoroethane is recycled as at least a part of the 2-halo-1,1,1-trifluoroethane provided to the reaction mixture and the 2,2,2-trifluoroethanol is recovered from the remainder of the withdrawn reaction product mixture.

In a preferred embodiment of the invention, the withdrawn reaction product mixture is provided with a temperature effective to form two phases, namely, a first phase containing the predominant amount of unreacted 2-halo-1,1,1-trifluoroethane and a second phase containing the predominant amount of the 2,2,2-trifluoroethanol in the hydroxylated compound, e.g., water. The first phase is separated from the second phase. The separated first phase is recycled as part of the 2-halo-1,1,1-trifluoroethane provided to the reaction mixture. The 2,2,2-trifluoroethanol is recovered from the second phase, e.g., by distillation.

In another aspect of the invention, the second phase can be treated with acid to convert the carboxylic acid salt therein to its carboxylic acid form. This carboxylic acid is then separated from the second phase and recycled, with the addition of base thereto to reform the carboxylic acid salt, as at least part of the carboxylic salt provided to the reaction mixture.

The process of the invention provides a number of distinct advantages. Specifically, the process of the invention can be performed continuously in one reactor without the need for isolation of the intermediate, i.e., 2,2,2-trifluoroethyl acetate. The reaction is fast and thus can be performed efficiently, i.e., a relatively high conversion can be obtained with relatively low residence times. Moreover, there is no need for agitation as in the Lawlor et al. patent or for special aprotic solvents as in the Astrologes patent. In addition, the process of the present invention allows internal recycling of unreacted 2-halo-1,1,1-trifluoroethane.

Moreover, in one aspect of the invention, such 2-halo-1,1,1-trifluoroethane can be recycled without distillation and therefore without the additional energy required. For example, by the process of the present invention employing phase separation, the phase containing the predominant amount of the unreacted 2- halo-1,1,1-trifluoroethane can be recycled to the reaction mixture under pressure. Such phase can, preferentially, be recycled internally by gravity flow.

Further, depending on the salt employed, the carboxylic acid salt can also be recycled by converting it to its acid form, distilling the acid, and then supplying this acid to a basic solution to reconvert it to the salt for supplying carboxylic acid salt to the reaction mixture.

Still further, the process of the invention can employ inexpensive non-agitated tubular reactors which makes the process economically advantageous. Because such inexpensive tubular reactors can be employed, the corrosivity of the reaction is not of as much concern as with batch reactors employing, for example, high pressure agitated autoclaves. In particular, the tubular reactors can be easily and relatively economically replaced when, as and if desired or necessary, rather than trying to prevent corrosion by employing more expensive corrosion resistant alloys.

The process of the invention also provides environmental advantages in that the primary products of the reaction can be the desired 2,2,2-trifluoroethanol and environmentally benign salt water. The other materials in the reaction such as the carboxylic acid salt and the unreacted 2-halo-1,1,1-trifluoroethane are preferably recycled. All of these advantages make the process of the invention economically and environmentally desirable.

DETAILED DESCRIPTION

Figure 1:
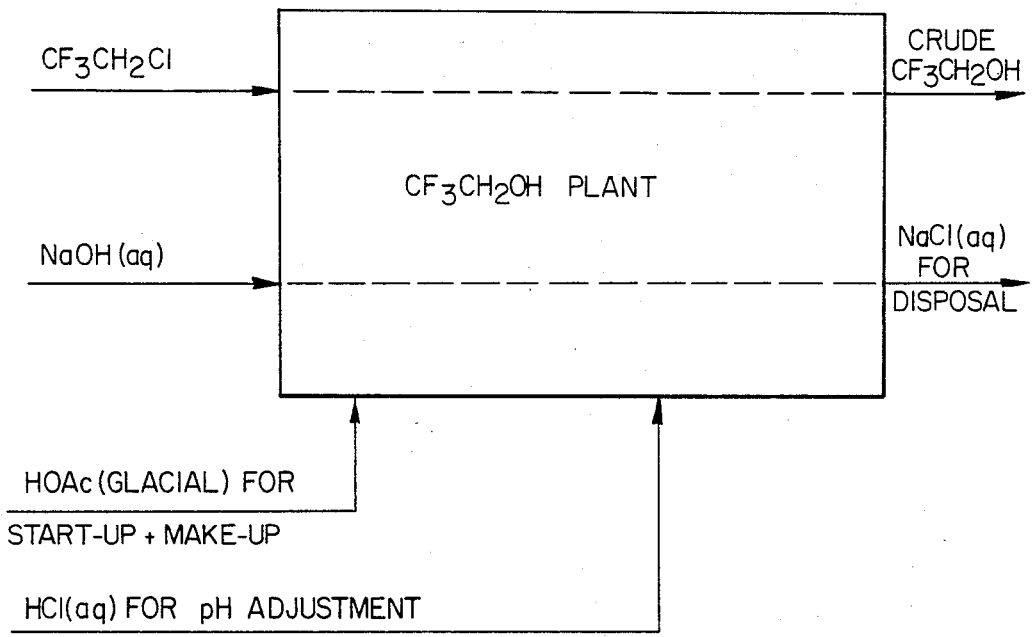
FIG. 1 is a block diagram broadly illustrating one embodiment of the process of the invention.

The process of the invention is a continuous process for preparing 2,2,2-trifluoroethanol. In this process, 2-halo-1,1,1,-trifluoroethane (preferably, 2-chloro-1,1,1-trifluoroethane, which is also known as fluorocarbon 133a), a salt of a carboxylic acid and an hydroxylated compound (preferably water) are continuously provided to a reaction mixture in a reactor. The general reaction can be illustrated as follows:

$$nCF_3CH_2X + (RCO_2)nM + nR'OH \rightarrow nCF_3CH_2OH + nRCO_2R' + MX_n$$

wherein X is an halogen selected from Cl, Br or I; R and R' are independently hydrogen or an organic moiety; M is an alkali or alkaline earth metal; and n is 1 or 2 depending on the valency of the M metal. For example, $(RCO_2)_nM$ can represent a carboxylic acid salt such as a formate, acetate, carbonate, etc; and R'OH can represent water or a glycol, etc.

The mechanism of the reaction employing 2-chloro-1,1,1-trifluoroethane, acetate salts and $H_2O$ has been studied extensively. We have found that the reaction is an exothermic, two step reaction involving an intermediate, 2,2,2-trifluoroethyl acetate ($CH_3CO_2CH_2CF_3$), which compound can be isolated from a reaction without the water. The mechanism can be illustrated by the following equations:

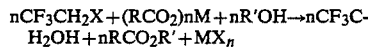
$$CF_3CH_2Cl + CH_3CO_2M \rightarrow CH_3CO_2CH_2CF_3 + MCl$$

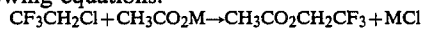
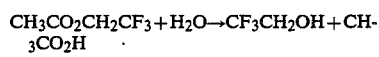
$$CH_3CO_2CH_2CF_3 + H_2O \rightarrow CF_3CH_2OH + CH_3CO_2H$$

wherein M is a alkali metal cation.

The process of the invention can be performed in any reactor suitable for continuous operation, i.e., those with continuous introduction of reactants and withdrawal of the reaction product mixture. Tubular reactors are preferred because of their convenience and relatively low cost. Preferably, the reactor, especially the reactor surface in contact with the reactants, is comprised of a corrosion resistant material such as Incoloy ® 825. The reactor can be packed or unpacked. For example, suitable materials for packing the reactor include polytetrafluoroethylene rings, metal packings, etc.

The 2-halo-1,1,1-trifluoroethane can be the chloro, bromo or iodo compound. The bromo and iodo groups are better "leaving" groups, but at this time these compounds are not as economically feasible in terms of availability and cost. The preferred compound is 2-chloro-1,1,1-trifluoroethane.

The hydroxylated compounds which can be employed in the present invention include any such hydroxylated compounds which will provide the necessary hydroxy group for hydroxylation or hydrolysis of the reactants to the desired 2,2,2-trifluoroethanol. Suitable hydroxylated compounds include, inter alia, water, alcohols and glycols. Examples of suitable alcohols and glycols include lower alcohols such as ethanol, ethylene glycol, propylene glycol and glycerine. Water is the preferred hydroxylated compound.

Suitable carboxylic acid salts for use in the present invention include sodium, potassium, manganese, zinc and magnesium salts of organic carboxylic acids, e.g., aliphatic and aromatic carboxylic acids. The salts should be soluble in the solution to be added to the reactor and also at the reaction temperature. Examples of suitable organic acid salts include salts of carbonic acid, formic acid, acetic acid, propionic acid, oleic acid, stearic acid, pelargonic acid, benzoic acid, phthalic acid and mixtures thereof. Preferably, the carboxylic acid is a liquid at ambient temperatures and does not substantially decompose at the reaction temperatures. Also, the carboxylic acid preferably can be distilled and recycled for further use in the reaction mixture as explained further below.

Preferred carboxylic acid salts include sodium acetate and potassium acetate. When potassium acetate and 2-chloro-1,1,1-trifluoroethane are employed, it is preferred to use a molar ratio of 2-chloro-1,1,1-trifluoroethane to potassium acetate of 1.0 or greater.

The 2-halo-1,1,1-trifluoroethane is generally added to the reactor as such, but also could be added as a solution, if desired. Suitable solvents could include any solvent that dissolves the 2-halo-1,1,1-trifluoroethane but does not react with any of the reactants or products or decompose at the reaction conditions.

A solvent can also be employed in addition to the reactants, if desired, or the reaction could be run without added solvent. The solvent need not be the same as the solvent, if any, for the 2-halo-1,1,1-trifluoroethane. Various solvents for the reaction mixture can be employed in the present invention. Suitable solvents include, for example, ethylene glycol diacetate, ethylene glycol dimethyl ether, or even the desired product itself, 2,2,2-trifluoroethanol.

The nature of the solvent can affect the multiphase behavior either of the reaction mixture at the reaction conditions and/or of the reaction product mixture after cooling. The solvent may provide complete miscibility of the reactants at reaction conditions, while still providing phase separation of the reaction product mixture upon cooling. For example, with water as both a reactant and a solvent, this miscibility can occur at the reaction conditions when the critical temperature of water is approached. Moreover, in general a solublization of the reaction mixture can occur when reaction conditions approach critical conditions of the hydroxylated compound with or without the presence of additional solvent. When the solvent employed provides an homogeneous reaction product mixture upon cooling, the recycle of reactants and/or recovery of the product can be performed by any suitable means well-known in the art, e.g., by distillation, solvent extraction, HPLC, etc.

The carboxylic acid salt is normally added as a solution, preferably dissolved in the hydroxylated compound, which in turn is preferably an aqueous solution having a pH of from about 3 to about 10. More preferably, the pH of the carboxlyic acid salt solution is from about 4 to about 7. The carboxylic acid solution can also be a buffered solution by employing a combination of the salt and its corresponding acid. The salt of the carboxylic acid can be formed in the reactor itself by adding a basic solution to the reactor along with a carboxylic acid or solution thereof. However, it is preferred, even when the carboxylic acid such as acetic acid is recycled, that the carboxylic acid first be mixed with a base or a solution thereof to form a solution of the carboxylic acid salt for addition to the reactor, rather than adding the base and acid separately, thus saving pumps, controls, piping, etc.

In a preferred embodiment of the invention, the reactants are pressurized and preheated prior to introduction into the reactor. The two reactant streams can be pressurized and heated by any suitable means conventional in the art, for example, by pressure pumps such as a LEWA metering pump and by heat exhange with hot oil, molten salt, fluidized solids, Dowtherm ® or any other high temperature heat transfer medium. Electrical heaters or direct fired heaters could also be used. The heat exchange system can be employed to add or remove heat from the system, depending, for example on the heat of reaction. Conventional pressure valves, pressure controllers and pressure transducers can also be used to control and monitor the pressure system as is known in the art.

In the process of the invention, the reactants are preferably supplied to the bottom of a vertically mounted tubular reactor so that the 2-halo-1,1,1-trifluoroethane is forced to pass through the hydroxylated component which is more dense at reaction temperature. Also, the process of the invention could employ a reflux-type system in which the 2-halo-1,1,1-trifluoroethane is condensed at the reaction pressure and recycled. The condensate, which can contain both the hydroxylated compound and the 2-halo-1,1,1-trifluoroethane, can also be cooled, collected and allowed to separate into two phases with the separated phases being recycled to the reactor.

The reactor is pressurized to a reaction pressure at or above the autogenously developed pressure of the reaction mixture itself. Preferably, the pressure in the reaction chamber is between about 750 psig and about the critical pressure of the hydroxylated compound, more preferably at least about 1000 psig, e.g., 1100–1400 psig.

The reactor is also at a reaction temperature of from about 223° C. to about the critical temperature of the hydroxylated compound. The lower temperature of this range represents the critical temperature for 2,2,2-trifluoroethanol. Since water is the preferred hydroxylated compound, the reaction temperature in this instance is in the range from about 223° C. to about 374° C. The upper limit of this range represents the critical temperature for water. Preferably, the reaction temperature is at least about 250° C., more preferably at least 270° C.

The temperature and pressure conditions are selected so that the 2-halo-1,1,1-trifluoroethane and the resulting product, 2,2,2-trifluoroethanol, both are above their critical temperatures and critical pressures. Also, these conditions are preferably selected so that the solvent for the carboxylic acid salt and/or the hydroxylated compound are also near or approaching their critical state. Thus, employing water as the hydroxylated compound and as the solvent for the carboxylic acid salt, it is preferred to operate at pressures above about 1000 psig and temperatures above about 250° C., more preferably, above about 270° C.

Since the unreacted 2-halo-1,1,1-trifluoroethane is recycled in the process of the invention, percent conversion per pass is of less significance than the overall yield per unit of time. Therefore, the reaction can be performed at higher temperatures with lower residence times to provide high yields. The reactants, i.e., the 2-halo-1,1,1-trifluoroethane, the carboxylic acid salt and the hydroxylated compound, are typically supplied to the reactor and passed through the reactor at a rate sufficient to provide an output (space velocity expressed as weight of 2,2,2-trifluoroethanol produced per hour per unit of reactor volume based on the superficial volume of the reactor) of at least about 40 grams/hour/liter, more preferably, at least about 100 grams/hour/liter. Outputs of 200 grams/hour/liter and higher of 2,2,2-trifluoroethanol have been obtained and even higher outputs are expected by optimization of the reaction conditions. Typically, with 2-halo-1,1,1-trifluoroethane, water and acetate salts, the optimum residence time is from about 28 to about 56 minutes based on the reactor superficial volume, i.e., based on an unpacked column. Actual residence times with packed columns are probably about one half of these times. Such residence times lead to high 2,2,2-trifluoroethanol space velocities (or outputs) and high 2,2,2-trifluoroethanol yields.

Under the above conditions with 2-chloro-1,1,1-trifluoroethane, water and acetate salt, it is believed that the reaction is taking place in the aqueous phase and that the rate of reaction depends upon the solubility of the 2-chloro-1,1,1-trifluoroethane in the carboxylic acid salt solution under the reaction conditions. As the critical state of water is approached, the reaction mixture appears to behave as an homogeneous fluid. Conducting the reaction under conditions in which the 2-chloro-1,1,1-trifluoroethane and 2,2,2-trifluoroethanol are above their critical temperatures at these pressures provides a dramatic change in solubility of these organic materials in the aqueous salt solutions. Similar results are expected with the bromo and iodo compounds. Our experiments indicate that excess, insoluble 2-chloro1,1,1-trifluoroethane merely passes through the reaction system without effect other than to maintain the aqueous phase in a saturated condition. It also reduces the available reaction volume.

The molar ratio of the carboxylic acid salt and the 2-halo-1,1,1-trifluoroethane supplied to the reactor affects the rate of reaction and thus the yield. Suitable molar ratios of added 2-chloro-1,1,1-trifluoroethane to carboxylic acid salt are from about 1:0.5 to about 1:10.0, more preferably from about 10.9 to about 1:1. Similar ratios may also be useful for 2-bromo-1,1,1-trifluoroethane and 2-iodo-1,1,1-trifluoroethane. The most economical use of reactants and highest 2,2,2-trifluoroethanol output per unit of time per unit of reactor volume are obtained by employing, for example, a feed of 2-chloro-1,1,1-trifluoroethane and sodium acetate salt in a molar ratio of as high as 1.4 with an optimum between 0.7 and 1.4. Employing potassium acetate as the carboxylic acid salt, it is, however, preferable to use a molar ratio of 2-chloro-1,1,1-trifluoroethane to potassium acetate of greater than 1.0

The carboxylic acid salt is preferably supplied to the reactor as a solution, most preferably, an aqueous solution. However, other solvents for the carboxylic acid salt can be employed so long as some hydroxylated compound is present, again preferably water. Moreover, a molten salt could be employed such as sodium acetate trihydrate. Thus, as used here and in the claims, the providing of a salt of a carboxylic acid and an hydroxylated compound to the reaction mixture is intended to include providing, for example, a molten hydrated salt, e.g., sodium acetate trihydrate. In this connection, it has been found that the hydroxylated compound is necessary to provide the desired end product. If the hydroxylated compound is not present, the ester, e.g., 2,2,2-trifluoroethyl acetate, can be isolated as the major product.

At least a portion of the reaction product mixture is continuously withdrawn from the reactor. In this connection, by reaction product mixture we mean to cover situations in which the reactants, products, etc. withdrawn from the reactor can be miscible or immiscible depending on, for example, the reactants and products themselves, the solvents employed, the temperature and pressure, etc. Thus, the reaction product "mixture" can be one phase or multiple phases. Typically, with a tubular reactor, the amount of reaction product mixture continuously withdrawn is determined by the rate of flow of the reactants into the reactor, i.e., the reaction product mixture exiting from the reactor which in turn is dependent on desired residence time for the reactants. Preferably, the reaction product mixture is withdrawn from the reactor under pressure, preferably the reaction pressure.

In the process of the invention, unreacted 2-halo-1,1,1-trifluoroethane is separated from the withdrawn reaction product mixture and recycled to the reactor as part of the 2-halo-1,1,1-trifluoroethane provided to the reaction mixture. The separation can be performed by any means suitable for use with a continuous process. For example, unreacted 2-halo-1,1,1-trifluoroethane can be distilled from the withdrawn reaction product mixture and recycled to the reaction mixture. Preferably, in the absence of an homogeneous solvent, however, the withdrawn reaction product mixture is provided with a temperature effective to form a first phase containing the predominant amount of unreacted 2-halo-1,1,1-trifluoroethane and a second phase containing the predominant amount of 2,2,2-trifluoroethanol. The two phases allow easy and efficient separation of most of the unreacted 2-halo-1,1,1-trifluoroethane for recycling. Moreover, the reaction pressure can be maintained during the phase separation, which allows internal recycling by simple gravity return flow.

Another significant finding of the process of the invention is that with 2-chloro-1,1,1-trifluoroethane, water and acetate salts, at temperatures of about 130° C. and about reaction pressures, a relative density inversion occurs. The phase containing the predominant amount of the unreacted 2-chloro-1,1,1-trifluoroethane is normally more dense than the product aqueous phase, while above this temperature it is less dense than the product aqueous phase. This density inversion has been found to be of great significance in the process of the invention. In particular, because of the density inversion as discussed above, the phase containing the predominant amount of unreacted 2-chloro-1,1,1-trifluoroethane can exist either as the upper or lower phase. Thus, the 2-chloro-1,1,1-trifluoroethane-containing phase is the upper phase at temperatures above about 130° C. under typical pressure conditions and is the lower phase at temperatures below about 130° C. under such pressure conditions. Accordingly, a temperature of the withdrawn reaction product mixture can be provided sufficient to form the phase containing the predominant amount of unreacted 2-chloro-1,1,1-trifluoroethane as either the top or bottom layer. Preferably, the fluid withdrawn from the reactor is cooled to below such inversion temperature to facilitate phase separation. In this connection, having the phase containing the predominant amount of the 2-chloro-1,1,1-trifluoroethane as the bottom layer facilitates phase separation in that this phase can be easily recycled to the reactor by simple gravity flow under the reaction pressure.

By employing a phase separation for separating the predominant amount of the unreacted 2-halo-1,1,1-trifluoroethane from what amounts to the remainder of the reaction product mixture, a number of advantages are obtained. In particular, there is no need to isolate the unreacted 2-halo-1,1,1-trifluoroethane, but rather it can be recycled internally (i.e., within the reactor system) under pressure. Moreover, no distillation or the energy required therefor is necessary to provide relatively pure unreacted 2-halo-1,1,1-trifluoroethane for recycling to the reactor. Thus, the continuous process of the invention employing such a phase separation and recycling provides an economically advantageous and highly efficient process for continuously preparing 2,2,2-trifluoroethanol.

Of course, it is understood that, because the process is a continuous one, the first and second phases are continually being formed and only a portion of the first phase is normally being recycled at any particular point in the continuous process. In other words, during the operation of the continuous process, there is almost always a first and second phase present in a collection chamber with a portion of the first phase continuously being withdrawn from such chamber for recycling to the reactor.

Especially in the start-up stages of the continuous process of the invention, the withdrawn reaction product mixture can contain relatively high amounts of unreacted 2-halo-1,1,1-trifluoroethane. Because 2,2,2-trifluoroethanol is not completely confined to the aqueous phase, under such conditions there may be little of the 2,2,2-trifluoroethanol in the aqueous phase. The relative amount of 2,2,2-trifluoroethanol does build up and therefore a greater amount is found in the aqueous phase. On the other hand, even when significant amounts of 2,2,2-trifluoroethane have been formed, the unreacted 2-halo-1,1,1-trifluoroethane will extract some 2,2,2-trifluoroethanol. Thus, it would be desirable to run the reaction with minimum 2-halo-1,1,1-trifuoroethane to be recycled, i.e., at maximum conversion of 2-halo-1,1,1-trifluoroethane.

The separation of the phases can be accomplished by any suitable means. For example, on the bench scale a sight window in a pipe tee can be used through which the separate phases can be observed. Preferably, the separation of the 2-halo-1,1,1-trifluoroethane containing phase is controlled automatically with a conventional interface level controller based on, e.g., nuclear, sonic, pressure change sensing or other appropriate phase sensing devices.

In a preferred embodiment of the invention, the carboxylic acid salt is recycled. For example, the second phase (normally aqueous) containing the predominant amount of the 2,2,2-trifluoroethanol product usually contains most, if not all, of the carboxylic acid salt. This second phase can be treated with acid, e.g. HCl to convert the salt back to the carboxylic acid form. The carboxylic acid can then be separated from the second phase by means conventional in the art. For example, if the acid is distillable, the acid can simply be distilled from the second phase and returned directly to the reactor as such. Alternatively, such distilled acid could be first mixed with a basic solution to convert the acid back to the salt form. This salt solution could then be added to the reactor. With some acids such as acetic acid, a saltingout effect can occur, so that a strong acetic acid solution can be distilled away from the rest of the aqueous phase.

If the acid is not distillable, it could for example be extracted from the second phase by an appropriate solvent. The acid could then be extracted from such solvent with a basic solution in which the soluble salt form of the acid would then be reformed. Again, such salt solution could be employed for supplying carboxylic acid salt to the reaction mixture. If phase separation is not employed, the acid (if distillable) could be fractionally distilled from the reaction product mixture. Moreover, if the acid is such that a significant portion is found in the first phase, it can be recycled with the first phase as discussed above.

The desired 2,2,2-trifluoroethanol product can be recovered by means conventional in the art. For example, the 2,2,2-trifluoroethanol can be distilled from the reaction product mixture withdrawn from the reactor. This distillation can take place either directly from such reaction product mixture or phase separation of one or more of the reactants or by-products can be first performed. For example, if the separation into the first and second phases as discussed above is performed, the 2,2,2-trifluoroethanol can be distilled from the second phase after separation from the first phase, thus avoiding the possibility of having to distill the unreacted 2-halo-1,1,1-trifluoroethane from the 2,2,2-trifluoroethanol and then redistilling the 2,2,2-trifluoroethanol. Moreover, the 2,2,2-trifluoroethanol can be distilled from such second phase either before or after addition of acid for recycling of the carboxylic acid salt. For example, if the carboxylic acid salt is acetate, hydrochloric or other acid can be added to the second phase to convert the acetate to acetic acid. The 2,2,2-trifluroethanol can be distilled either prior to the addition of the acid or can be fractionally distilled with the acetic acid produced after the addition of such acid.

Preferably, the process of the invention is performed so that the recycled unreacted 2-halo-1,1,1-trifluoroethane is under pressure, preferably, the reaction pressure. Thus, in the process of the invention, the continuous withdrawing step, the temperature providing step to provide the first and second phases, the separating of the first and second phases, and the recycling of the separated first phase to the reaction mixture are performed under pressure, preferably the reaction pressure. Moreover, the withdrawing, temperature providing, separating and recycling steps are performed continuously.

FIG. 1 broadly illustrates the process of the invention by employing 2-chloro-1,1,1-trifluoroethane as the 2-halo-1,1,1-trifluoroethane, sodium acetate as the salt and water as the hydroxylated compound FIG. 1 represents the trifluoroethanol plant in the process of the invention. All that needs to be supplied to the plant are the 2-chloro-1,1,1-trifluoroethane, base, (e.g., sodium hydroxide preferably in a minimum amount approaching the stoichiometric equivalent), any necessary acetic acid (preferably glacial) for startup and/or makeup, and any necessary acid such as hydrochloric acid for pH adjustment. Thus, in the trifluoroethanol plant (FIG. 1), the acetate salt is internally recycled as is any unreacted 2-chloro-1,1,1-trifluoroethane. Thus, crude 2,2,2-trifluoroethanol and salt solution such as sodium chloride solution are essentially the only materials withdrawn from the plant 1. The environmental advantages of this process are clear, since basically only the desired end product and the relatively environmentally benign sodium chloride solution are produced.

Figure 2:
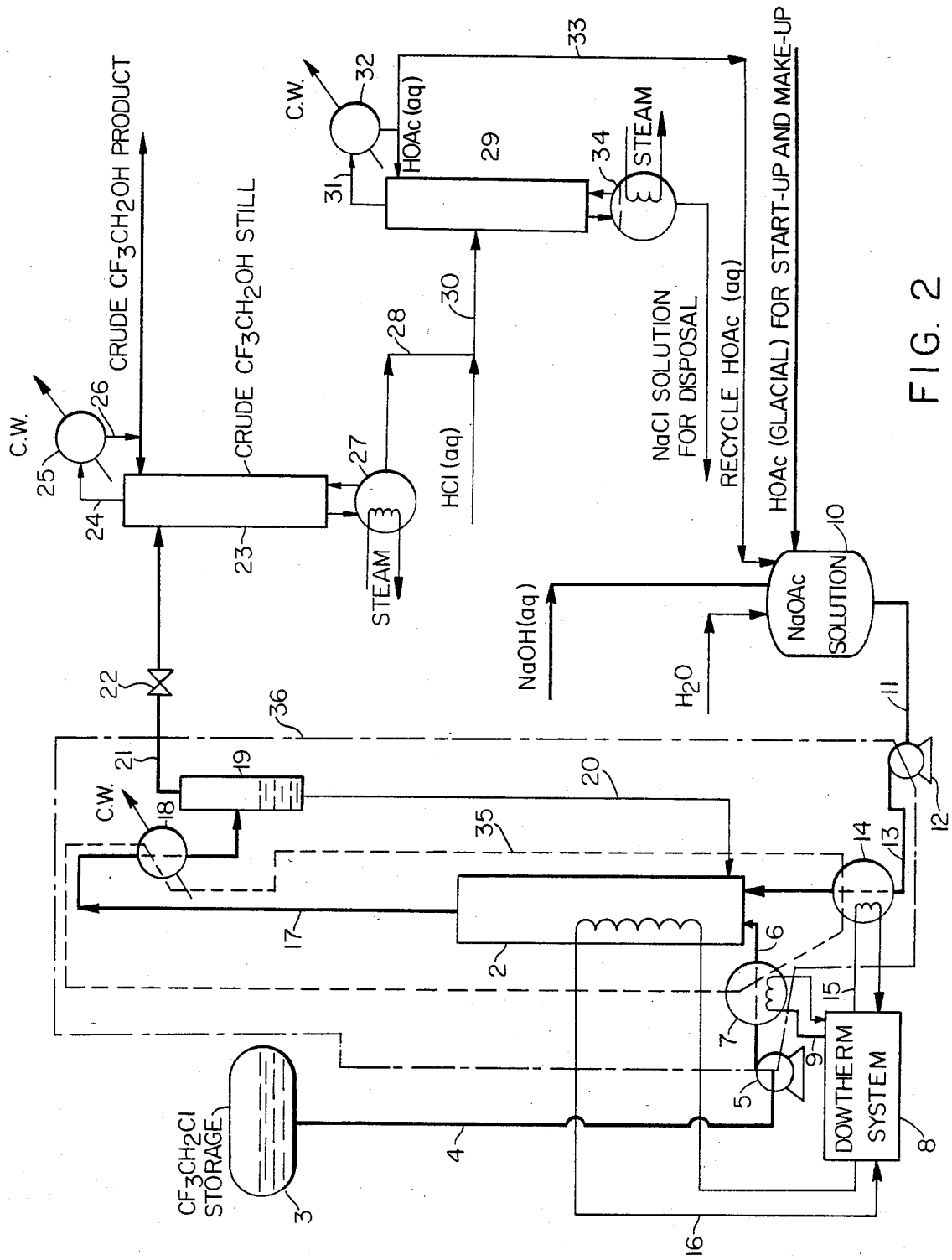
FIG. 2 is a schematic representation of a system for performing one embodiment of the process of the invention.

A more detailed illustration of one embodiment of the invention is provided in FIG. 2. In the system illustrated in FIG. 2, the process is again illustrated in connection with a process employing some preferred reactants, i.e, 2-chloro-1,1,1-trifluoroethane and aqueous sodium acetate. The input of reactants and the output of product are shown in darker lines in FIG. 2.

The 2-chloro-1,1,1-trifluoroethane is provided to the reactor 2 from a storage tank 3 which is normally under pressure because of the low boiling point of the starting material. The 2-chloro-1,1,1-trifluoroethane is supplied via line 4, pump 5 (which further pressurizes the 2-chloro-1,1,1-trifluoroethane) and line 6 which passes through an appropriate heat exchanger 7, which in the embodiment shown employs a Dowtherm ® system 8 as the high temperature heat exchange medium for the heat exchanger via line 9. The pump 5 can be any suitable pump for providing the high pressure such as a LEWA metering pump. Suitable pressure valves and pressure transducers can be employed to control and monitor the pressure.

The aqueous sodium acetate solution is supplied to the reactor 2 from storage tank 10 via line 11, pump 12, and line 13 which passes through heat exchanger 14. Again, any conventional heat exchanger and pump to provide the high temperature and pressure desired can be employed. In the embodiment shown, the heat exchanger 14 is supplied with high temperature heat exchange medium from the Dowtherm ® system via line 15.

The sodium acetate can be added to the storage tank 10 as such or can be prepared by mixing aqueous sodium hydroxide and acetic acid supplied either as glacial acetic acid for startup and makeup or via recycled acetic acid as discussed above.

The temperature of the reactor 2 is also controlled. In the embodiment shown, this temperature is controlled by the heat exchange fluid supplied to the reactor 2 via line 16 from the Downtherm ® system 8. Because the reaction is exothermic, this heat exchange in the reactor may either heat or cool the reactor when and as necessary.

The reactor 2 can be either packed or unpacked, as desired. In the reactor, the temperature and pressure of the reaction mixture are controlled so that the reaction temperature is between about 223° C. and the critical temperature in this instance of water (i.e., 374° C.) and the reaction pressure is from about 750 psig to about the critical pressure of the water and in most instances above 1000 psig.

The density inversion described above occurs in reactor 2. Specifically, the 2-chloro-1,1,1-trifluoroethane is normally more dense than water. However, because of the density inversion at higher temperatures, the 2-chloro-1,1,1-trifluoroethane supercritical fluid is less dense than water in the reactor. The vertical tubular reactor facilitates the reaction because of this density inversion, as shown in FIG. 2, since the 2-chloro-1,1,1-trifluoroethane is forced to pass through the more dense aqueous components.

The reaction product mixture is withdrawn from the reactor 2 via line 17 and in the embodiment shown is led at essentially reaction temperature to the top of a cold water condenser 18 and cooled to a suitable temperature for the formation of two phases. The cooled reaction product mixture is collected in tank 19 where the first and second phases form. In this instance, if the temperature of the reaction product mixture in collection tank 19 is below about 130° C., the bottom phase (first phase) will contain the predominant amount of unreacted 2-chloro-1,1,1-trifluoroethane, while the top aqueous phase (second phase) will contain the predominant amount of the desired 2,2,2-trifluoroethanol product.

In the embodiment shown, the 2-chloro-1,1,1-trifluoroethane can be separated from the aqueous phase containing most of the 2,2,2-trifluoroethanol by simple phase separation. The first phase can then be returned to the reaction mixture in the reactor 2 by gravity flow via line 20.

The second phase containing the predominant amount of the 2,2,2-trifluoroethanol product can be withdrawn from the collection tank 19 via line 21 through a pressure reduction valve 22. In the embodiment shown, the second phase is directly distilled in a still 23, with the crude 2,2,2-trifluoroethanol product being collected through line 24 via a cold water condenser 25 and line 26. The still can be heated, for example, via a steam heat exchanger 27 or in any other conventional manner. The residue from the still 23 is collected via line 28 and passed to a second still 29 via line 30. Acid such as hydrochloric acid can be added to the still 29, for example, via line 30 to convert acetate salt to its acetic acid form. In the still 29, the acetic acid is distilled and collected via line 31 and cold water condenser 32. The aqueous acetic acid obtained can be recycled to the sodium acetate storage tank 10 via line 33. The still 29 can be heated by any conventional heat exchange system and in the instance shown the still employs a steam heat exchange system 34.

Essentially, the only product collected from the bottom of still 29 is a sodium chloride solution which is relatively environmentally benign. This material can be treated, if desired, to recover the sodium chloride or can be disposed of as is.

The dotted line 35 is intended to illustrate where in the reactor system the reactor temperature is maintained. while dashed line 36 is intended to represent the areas in the reactor system where reaction pressure is maintained.

The following examples are intended to illustrate, but not to limit, the process of the invention.

EXAMPLE 1

A 42 inch long unpacked, Ni alloy, tubular reactor (of which 32 inches were in an electric furnace) was mounted vertically. The reactor tube was 1 inch O.D. by 0.065 inch wall thickness. A 5 inch section of the tube above the furnace was insulated. The reactor was pressurized to about 1250-1350 psig with deionized water and then the system was heated to about 20° C. below the reaction temperature to allow for the subsequent expected exotherm. An aqueous 30% by weight sodium acetate solution at pH 6 and the 2-chloro-1,1,1-trifluoroethane were fed into the bottom of the tubular reactor independently and continuously via a dual head metering pump. The reaction mixture supplied to the reactor was preheated by a heating tape on the feed lines. The reaction took place in the reactor without agitation. Temperatures of the reactor were controlled by two manually adjusting powerstats for two zones of the reactor furnace and by an automatic system, which included a digital temperature controller, an amperage controller (SCR) and by a thermocouple for the third zone. The controlling thermocouple was located in the last zone of the furnace. Thus, the temperature and pressure during the various runs were controlled as indicated in Table 1 below.

The fluid exited the reactor through a water-cooled phase separator. The top aqueous phase was transferred automatically through a pressure let down system into three low pressure traps in series. The first trap was at ambient temperature, the second trap was at 0° C., and the third was at −78° C.

The bottom organic phase was manually transferred through two metering valves into the second trap described above. All the collected materials in the three traps were analyzed by gas chromatography. The products were collected at constant time intervals as again set forth in Table 1 below. The feed rate of the 2-chloro1,1,1-trifluoroethane and sodium acetate solution, the residence time, the molar ratios of 2-chloro-1,1,1-trifluoroethane to sodium acetate and water, the pH of the sodium acetate solution, the total reaction time, the product collection time, conversion percent, yield percent and output for the various runs are as indicated in Table 1 below.

TABLE 1

| Run No. | Temp., °C. | Press. psig. | Feed Rate, gm/min. TFEC[1] | Feed Rate, gm/min. NaOAc Sol'n | Residence Time, Min.[4] | Molar Ratio TFEC | Molar Ratio NaOAc | Molar Ratio Water | pH of NaOAc Sol'n | Total Run Time, Hrs. | Prod. Collec. Time Hrs.[5] | TFE[2] Product Conversion % | TFE[2] Product Yield % | Output[3] gm/hr/l |
|---|---|---|---|---|---|---|---|---|---|---|---|---|---|---|
| 1 | 249-287 | 1300 | 0.8 | 5.2 | 56 | 1.0 | 2.8 | 26.8 | 6.0 | 6.4 | 2.5 | 76.6 | 95.1 | 95.8 |
| 2 | 249-286 | 1300 | 0.5 | 6.0 | 51 | 1.0 | 5.4 | 53.6 | 6.0 | 5.4 | 2.7 | 64.7 | 73.2 | 55.6 |

TABLE 1-continued

| Run No. | Temp., °C. | Press. psig. | Feed Rate, gm/min. TFEC[1] | Feed Rate, gm/min. NaOAc Sol'n | Residence Time, Min.[4] | Molar Ratio TFEC | Molar Ratio NaOAc | Molar Ratio Water | pH of NaOAc Sol'n | Total Run Time, Hrs. | Prod. Collec. Time Hrs.[5] | TFE[2] Product Conversion % | TFE[2] Product Yield % | TFE[2] Product Output[3] gm/hr/l |
|---|---|---|---|---|---|---|---|---|---|---|---|---|---|---|
| 3 | 250–288 | 1300 | 1.7 | 4.3 | 57 | 1.0 | 1.1 | 11.2 | 6.0 | 6.2 | 3.5 | 38.9 | 75.8 | 107.3 |
| 4 | 250–285 | 1300 | 1.9 | 3.1 | 68 | 1.0 | 0.7 | 6.9 | 6.0 | 6.1 | 3.0 | 28.1 | 93.1 | 97.1 |
| 5 | 255–286 | 1300 | 3.2 | 8.5 | 29 | 1.0 | 1.2 | 11.6 | 6.0 | 5.6 | 2.3 | 26.0 | 85.3 | 146.7 |

[1]TFEC = 2-chloro-1,1,1-trifluoroethane
[2]TFE = 2,2,2-trifluoroethanol
[3]TFE output or space velocity expressed as TFE produced in grams/hour/liter.
[4]Based on empty reactor and room temperature density.
[5]At steady state.

EXAMPLE 2

A series of experiments were run in accordance with a procedure similar to that described in Example 1. The reactor was, however, replaced by a vertical tubular reactor packed with 7 millimeter borosilicate glass Raschig rings, 0.16 inch stainless steel 316 "protruded" column packing, or 5/32 inch O.D. by 3/32 inch I.D. by ⅛ inch long polytetrafluoroethylene rings. In addition, in one run a recycle system for unreacted 2-chloro-1,1,1-trifluoroethane was employed in which the 2-chloro-1,1,1-trifluoroethane from the cooled and collected product mixture was returned to the reactor via the LEWA pump. The top portion of the reactor was insulated with black foamed glass insulation.

The reaction conditions and results were as set forth in Table 2 below. The residence times and 2,2,2-trifluoroethanol output were calculated based upon the superficial volume (without packings) of the reactor.

TABLE 2

| Run No. | Temp., °C. | Press. psig. | Feed Rate, gm/min. TFEC[1] | Feed Rate, gm/min. NaOAc Sol'n | Residence Time, Min.[4] | Molar Ratio TFEC | Molar Ratio NaOAc | Molar Ratio Water | Reactor Packing | Total Run Time, Hrs. | Prod. Collec. Time Hrs.[5] | TFE[2] Product Conversion % | TFE[2] Product Yield % | TFE[2] Product Output[3] gm/hr/l |
|---|---|---|---|---|---|---|---|---|---|---|---|---|---|---|
| 1 | 249–292 | 1300 | 1.7 | 4.3 | 56 | 1.0 | 1.1 | 11.1 | Glass Rings | 4.0 | 1.4 | 52.2 | >95 | 128.6 |
| 2 | 246–298 | 1295 | 3.5 | 8.6 | 28 | 1.0 | 1.1 | 10.5 | Metal Packing | 4.2 | 2.0 | 36.3 | 89.4 | 227.6 |
| 3 | 232–286 | 1300 | 3.2 | 8.7 | 28 | 1.0 | 1.2 | 11.8 | Metal Packing | 4.5 | 2.0 | 31.0 | 85.9 | 176.0 |
| 4[6] | 232–295 | 1300 | 3.2 | 8.8 | 28 | 1.0 | 1.2 | 11.8 | Metal Packing | 5.4 | 2.0 | 56.2 | 85.0 | 124.8 |
| 5 | 235–291 | 1300 | 2.4 | 6.0 | 41 | 1.0 | 1.1 | 10.5 | PTFE[7] Rings | 5.7 | 2.8 | 27.5 | 78.6 | 119.4 |
| 6 | 243–295 | 1300 | 1.6 | 4.4 | 56 | 1.0 | 1.2 | 11.4 | PTFE[7] Rings | 6.6 | 3.0 | 41.1 | 89.5 | 121.3 |
| 7 | 284–328 | 1305 | 2.5 | 6.2 | 39 | 1.0 | 1.1 | 10.2 | PTFE[7] Rings | 5.3 | 2.8 | 38.0 | 75.2 | 167.6 |
| 8 | 254–336 | 1305 | 1.7 | 4.3 | 56 | 1.0 | 1.1 | 10.2 | PTFE[7] Rings | 6.0 | 3.0 | 39.7 | 88.3 | 122.9 |

[6]Internal recycle of TFEC was exercised.
[7]PTFE = polytetrafluoroethylene.

EXAMPLE 3

Employing the procedure set forth in Example 2 above, aqueous potassium acetate solution was employed instead of sodium acetate solution. The tubular reactor was packed with polytetrafluoroethylene rings. The potassium acetate was the limiting reagent and an excess of 2-chloro-1,1,1-trifluoroethane was introduced. The reaction conditions and the results thereof are set forth in Table 3 below.

TABLE 3

| Run No. | Temp., °C. | Press. psig. | Feed Rate, gm/min. TFEC[1] | Feed Rate, gm/min. KOAc Sol'n | Residence Time, Min.[4] | Molar Ratio TFEC | Molar Ratio KOAc | Molar Ratio Water | pH of KOAc Sol'n | Total Run Time, Hrs. | Prod. Collec. Time Hrs.[5] | TFE[2] Product Conversion % | TFE[2] Product Yield % | TFE[2] Product Output[3] gm/hr/l |
|---|---|---|---|---|---|---|---|---|---|---|---|---|---|---|
| 1[8] | 242–300 | 1300 | 2.3 | 4.4 | 51 | 1.0 | 0.7 | 7.8 | 6.3 | 3.5 | 1.4 | 37.3 (54.1)[10] | 95.5 | 154.2 |
| 2[9] | 275–320 | 1305 | 1.3 | 4.0 | 62 | 1.0 | 0.8 | 15.5 | 6.0 | 6.3 | 3.2 | 43.1 (56.7)[10] | 84.0 | 97.6 |

[8]Potassium acetate solution used was 30% by weight.
[9]Potassium acetate solution used was 20% by weight.
[10]Conversion based on KOAc, the limiting reagent.

EXAMPLE 4

A series of reactions were carried out in a manner similar to Example 1 above in a unpacked, horizontally mounted tubular reactor, e.g., an Incoloy ® 825 tube, with a 1 inch O.D. and 0.87 inch I.D. The middle 32 inches of the 48 inches overall length were inside the electric furnace to control the reaction temperature. Three graphite packed metering valves in series were used as a pressure let-down system to reduce the pressure on the reaction product mixture. The reactor was pre-filled with deionized water. A dual head metering pump was used to reach the desired pressure. The system was preheated to the reaction temperature of at least 225° C. A 30% aqueous sodium acetate solution at a certain pH value, and 2chloro-1,1,1-trifluoroethane were fed independently and continuously by the metering pump into the tubular reactor. The reaction took place in the heated tube without additional agitation. The reaction temperature was automatically controlled by a digital temperature controller, and an amperage controller (SCR) sensing a thermocouple inserted axially into the tube to the center of the heated section. The pressure was manually controlled by adjusting the three metering valves. The exit stream was air-cooled and was collected continuously in three consecutive traps in which the first was at ambient temperature, the second was at 0° C. and the third was at −78° C. The collected materials in all three traps were analyzed by gas chromatography. The reaction conditions and the results of the reactions are reported in Table 4 below.

ously recycling the separated unreacted 2-halo-1,1,1-trifluoroethane as a part of the 2-halo-1,1,1-trifluoroethane provided to the reaction mixture, wherein said withdrawing, separating, and recycling are performed under pressure; and recovering the 2,2,2-trifluoroethanol from the remainder of the withdrawn reaction product mixture.

2. A process according to claim 1, wherein the 2-halo-1,1,1-trifluoroethane is 2-chloro-1,1,1-trifluoroethane.

3. A process according to claim 2, wherein said continuous separation of unreacted 2-chloro-1,1,1-triflouroethane from the withdrawn reaction product mixture is performed by fractional distillation.

4. A process according to claim 2, wherein the carboxylic acid salt is provided to the reactor by mixing a carboxylic acid with a basic solution and supplying the resulting solution at a pH of from 3 to 10 to the reaction mixture.

5. A process according to claim 2, wherein said hydroxylated compound comprises water.

6. A process according to claim 5, wherein the reaction temperature is in the range of from about 223° C. to about 374° C.

7. A process according to claim 1, wherein the pressure is at or near the reaction pressure.

8. A process according to claim 2, wherein the 2-

TABLE 4

| Run No. | Temp., °C. | Press. psig. | Feed Rate, gm/min. TFEC[1] | Feed Rate, gm/min. NaOAc Sol'n | Residence Time Min.[4] | Molar Ratio TFEC | Molar Ratio NaOAc | Molar Ratio Water | pH of NaOAc Sol'n | Total Run Time, Hrs. | Prod. Collec. Time Hrs.[5] | TFE[2] Product Conversion % | TFE[2] Product Yield % |
|---|---|---|---|---|---|---|---|---|---|---|---|---|---|
| 1 | 258 | 1120 | 0.8 | 5.0 | 55 | 1.0 | 2.7 | 27.9 | 7.2 | 4.1 | 3.0 | 53.2 | 99.4 |
| 2 | 258 | 750 | 1.3 | 5.7 | 46 | 1.0 | 1.9 | 19.8 | 7.2 | 4.1 | 3.0 | 7.4 | >90 |
| 3 | 258 | 1375 | 0.8 | 4.6 | 59 | 1.0 | 2.4 | 23.7 | 6.2 | 5.0 | 3.0 | 60.1 | 73.5 |
| 4 | 259 | 1350 | 0.9 | 4.7 | 57 | 1.0 | 2.2 | 21.5 | 5.6 | 5.0 | 3.0 | 49.4 | 72.2 |
| 5 | 258 | 1370 | 0.8 | 5.0 | 54 | 1.0 | 2.5 | 25.6 | 5.9 | 5.5 | 3.0 | 65.0 | 90.8 |
| 6 | 259 | 1350 | 0.8 | 4.8 | 56 | 1.0 | 2.5 | 24.5 | 6.0 | 23.8 | 18.0 | 68.0 | 93.4 |
| 7[11] | 269 | 1350 | 0.9 | 4.6 | 58 | 1.0 | 2.1 | 21.1 | 6.0 | 5.1 | 3.0 | 62.8 | 89.3 |
| 8[11] | 277 | 1350 | 0.8 | 4.7 | 58 | 1.0 | 2.7 | 26.7 | 6.0 | 5.2 | 3.0 | 77.0 | 91.1 |
| 9[11] | 278 | 1350 | 0.9 | 4.5 | 59 | 1.0 | 2.1 | 21.0 | 6.0 | 5.7 | 3.0 | 74.1 | 93.6 |
| 10[11] | 288 | 1350 | 0.9 | 4.9 | 54 | 1.0 | 2.2 | 22.1 | 6.0 | 5.0 | 3.0 | 67.8 | 93.4 |
| 11[11] | 277 | 1350 | 1.1 | 6.4 | 43 | 1.0 | 2.6 | 25.2 | 6.0 | 4.6 | 2.7 | 64.0 | 85.4 |

[11] Incoloy ® 825 was employed.

It will be understood that the embodiments described above are merely exemplary and that persons skilled in the art may make many variations and modifications without departing from the spirit and scope of the invention. All such modifications and variations are intended to be included within the scope of the invention as defined by the appended claims.

What is claimed is:

1. A continuous process for preparing 2,2,2-trifluoroethanol, said process comprising the steps of continuously providing 2-halo-1,1,1-trifluoroethane, a salt of a carboxylic acid and a hydroxylated compound to a reaction mixture in a reactor, wherein halo is selected from the group consisting of chloro, bromo and iodo; reacting said 2-halo-1,1,1-trifluoroethane, said carboxylic acid salt and said hydroxylated compound in said reactor at a reaction pressure at or above the autogenously developed pressure and at a reaction temperature of from about 223° C. to about the critical temperature of said hydroxylated compound thereby producing a reaction product mixture containing 2,2,2-trifluoroethanol; continuously withdrawing at least a portion of the reaction product mixture from the reactor; continuously separating unreacted 2-halo-1,1,1-trifluoroethane from the withdrawn reaction product mixture; continuchloro-1,1,1-trifluoroethane and the carboxylic acid salt are provided to the reaction mixture in a molar ratio of from about 1:0.5 to about 1:10.0.

9. A process according to claim 2, wherein the 2-chloro-1,1,1-trifluoroethane and the carboxylic acid salt are provided to the reaction mixture in a molar ratio of from about 1:0.9 to about 1:1.1.

10. A process according to claim 2, wherein said carboxylic acid salt is sodium acetate.

11. A process according to claim 2, wherein said carboxylic acid salt is potassium acetate.

12. A process according to claim 11, wherein the molar ratio of 2-chloro-1,1,1-trifluoroethane to potassium acetate provided to said reactor is 1.0 or greater.

13. A process according to claim 2, wherein the reaction temperature is at least about 250° C.

14. A process according to claim 2, wherein the reaction temperature is at least about 270° C.

15. A process according to claim 2, wherein the reaction pressure is from about 750 psig to about the critical pressure of said hydroxylated compound.

16. A process according to claim 2, wherein the reaction pressure is at least about 1000 psig.

17. A continuous process for preparing 2,2,2-trifluoroethanol, said process comprising the steps of continuously providing 2-halo-1,1,1-trifluoroethane, a salt of a carboxylic acid and a hydroxylated compound to a reaction mixture in a reactor, wherein halo is selected from the group consisting of chloro, bromo and iodo; reacting said 2-halo-1,1,1-trifluoroethane, said carboxylic acid salt and said hydroxylated compound in said reactor at a reaction pressure at or above the autogenously developed pressure and at a reaction temperature of from about 223° C. to about the critical temperrature of said hydroxylated compound thereby producing a reaction product mixture containing 2,2,2,-trifluoroethanol; continuously withdrawing at least a portion of the reaction product mixture from the reactor, providing a temperature of the withdrawn reaction product mixture effective to form a first phase containing the predominant amount of unreacted 2-halo-1,1,1-trifluoroethane and a second phase containing the predominant amount of the 2,2,2-trifluoroethanol; separating at least part of the first phase from the second phase; recycling the separated first phase as a part of the 2-halo-1,1,1-trifluoroethane provided to the reaction mixture, wherein said withdrawing, separating, and recycling are performed under pressure; and recovering the 2,2,2-trifluoroethanol from the second phase.

18. A process according to claim 17, wherein the 2-halo-1,1,1-trifluoroethane is 2-chloro-1,1,1-trifluoroethane.

19. A process according to claim 18, wherein the carboxylic acid salt is provided to the reactor by mixing a carboxylic acid with a basic solution and supplying the resulting solution at a pH of from 3 to 10 to the reaction mixture.

20. A process according to claim 18, wherein said hydroxylated compound comprises water.

21. A process according to claim 20, wherein the reaction temperature is in the range of from about 223° C. to about 374° C.

22. A process according to claim 18, wherein the pressure is at or near the reaction pressure.

23. A process according to claim 22, wherein the temperature of the withdrawn reaction product mixture is such that the first phase is the upper phase.

24. A process according to claim 22, wherein the temperature of the withdrawn reaction product mixture is such that the first phase is the bottom phase.

25. A process according to claim 24, wherein the first phase is recycled to the reaction mixture by gravity flow.

26. A process according to claim 18, wherein the 2-chloro-1,1,1-trifluoroethane and the carboxylic acid salt are provided to the reaction mixture in a molar ratio of from about 1:0.5 to about 1:10.0.

27. A process according to claim 18, wherein the 2-chloro-1,1,1-trifluoroethane and the carboxylic acid salt are provided to the reaction mixture in a molar ratio of from about 1:0.9 to about 1:1.1.

28. A process according to claim 18, wherein said carboxylic acid salt is sodium acetate.

29. A process according to claim 18, wherein said carboxylic acid salt is potassium acetate.

30. A process according to claim 29, wherein the molar ratio of 2-chloro-1,1,1,-trifluoroethane to potassium acetate provided to said reactor is 1.0 or greater.

31. A process according claim 18, wherein the reaction temperature is at least about 250° C.

32. A process according to claim 18, wherein the reaction temperature is at least about 270° C.

33. A process according to claim 18, wherein the reaction pressure is from about 750 psig to about the critical pressure of said hydroxylated compound.

34. A process according to claim 18, wherein the reaction pressure is at least about 1000 psig.

35. A continuous process for preparing 2,2,2-trifluoroethanol, said process comprising the steps of continuously providing 2-halo-1,1,1,-trifluoroethane, a salt of a carboxylic acid and a hydroxylated compound to a reaction mixture in a reactor, wherein halo is selected from the group consisting of chloro, bromo and iodo; reacting said 2-halo-1,1,1-trifluoroethane, said salt of the carboxylic acid and said hydroxylated compound in said reactor at a reaction pressure at or above the autogenously developed pressure and at a reaction temperature of from about 223° C. to about the critical temperature of the hydroxylated compound thereby producing a reaction product mixture containing 2,2,2,-trifluoroethanol; continously withdrawing at least a portion of the reaction product mixture from the reactor; providing a temperature of the withdrawn reaction product mixture effective to form a first phase containing the predominant amount of unreacted 2-halo-1,1,1-trifluoroethane and a second phase containing the predominant amount of the 2,2,2-trifluoroethanol; separating the first phase from the second phase; recycling the first phase as a part of the 2-halo-1,1,1-trifluoroethane provided to the reaction mixture, wherein said withdrawing, separating, and recyling are performed under pressure; treating said second phase with acid to convert the carboxylic acid salt therein to its carboxylic acid form; separating carboxylic acid from the second phase; recyling said carboxylic acid, with addition of a base to reform said carboxylic acid salt, as at least part of the carboxylic acid salt provided to the reaction mixture for said reaction with 2-halo-1,1,1-trifluoroethane; and recovering 2,2,2-trifluoroethanol from said second phase.

36. A process according to claim 35, wherein the 2-halo-1,1,1-trifluoroethane is 2-chloro-1,1,1-trifluoroethane.

37. A process according to claim 35, wherein the carboxylic acid is distillable and the carboxylic acid is separated from the second phase by distillation.

38. A process according to claim 37, wherein the carboxylic acid salt is provided to the reaction mixture by mixing a solution of the recycled carboxylic acid with a basic solution to form said carboxylic acid salt and supplying the resulting solution at a pH of from 3 to 10 to the reaction mixture.

39. A process according to claim 36, wherein said hydroxylated compound comprises water.

40. A process according to claim 39, wherein the reaction temperature is between about 223° C. and about 374° C.

41. A process according to claim 36, wherein the pressure is at or near the reaction pressure.

42. A process according to claim 36, wherein the temperature of the withdrawn reaction product mixture is such that the first phase is the upper phase.

43. A process according to claim 42, wherein the first phase is recycled to the reaction mixture by gravity flow.

44. A process according to claim 36, wherein the temperature of the withdrawn reaction product mixture is such that the first phase is the bottom phase.

45. A process according to claim 44, wherein the first phase is recycled to the reaction mixture by gravity flow.

46. A process according to claim 36, wherein the 2-chloro-1,1,1-trifluoroethane and the carboxylic acid salt are provided to the reaction mixture in a molar ratio of from about 1:0.5 to about 1:10.0.

47. A process according to claim 36, wherein the 2-chloro-1,1,1-trifluoroethane and the carboxylic acid salt are provided to the reaction mixture in a molar ratio of from about 1:0.9 to about 1:1.1.

48. A process according to claim 36, wherein said carboxylic acid salt is sodium acetate.

49. A process according to claim 36, wherein said carboxylic acid salt is potassium acetate.

50. A process according to claim 49, wherein the ratio of 2-chloro-1,1,1-trifluroethane to potassium acetate provided to said reactor is 1.0 or greater.

51. A process according to claim 36, wherein the reaction temperature is at least about 250° C.

52. A process according to claim 36, wherein the reaction temperature is at least about 270° C.

53. A process according to claim 36, wherein the reaction pressure is from about 750 psig to about the critical pressure for the hydroxylated compound.

54. A process according to claim 36, wherein the reaction pressure is at least about 1000 psig.

* * * * *